US00PP26005P2

(12) United States Plant Patent
Rutten

(10) Patent No.: US PP26,005 P2
(45) Date of Patent: Oct. 20, 2015

(54) ***HYDRANGEA* PLANT NAMED 'WIMS RED'**

(50) Latin Name: *Hydrangea paniculata*
Varietal Denomination: WIMS RED

(71) Applicant: Jan Oprins, Rijkevorsel (BE)

(72) Inventor: Wim A. M. Rutten, Leende (NL)

(73) Assignee: Jan Oprins, Rijkevorsel (BE)

( * ) Notice: Subject to any disclaimer, the term of this patent is extended or adjusted under 35 U.S.C. 154(b) by 183 days.

(21) Appl. No.: 13/987,209

(22) Filed: Jul. 11, 2013

Related U.S. Application Data

(60) Provisional application No. 61/743,332, filed on Aug. 31, 2012.

(51) Int. Cl.
*A01H 5/02* (2006.01)

(52) U.S. Cl.
USPC ..... Plt./250

(58) Field of Classification Search
USPC ..... Plt./250
See application file for complete search history.

(56) References Cited

PUBLICATIONS

UPOV—International Union for the Protection of New Varieties of Plants; PLUTO:Plant Varity Database; retrieved Feb. 28, 2015; culivar 'Wims Red' (1 page total).*
"New Plants and Flowers" web page http://www.newplantsandflowers.com/hydrangea-wims-red-turns-from-white-to-red/; retrieved Mar. 2, 2015 (2 pages total).*

* cited by examiner

*Primary Examiner* — Susan McCormick Ewoldt
(74) *Attorney, Agent, or Firm* — Penny J. Aguirre

(57) ABSTRACT

A new cultivar of *Hydrangea macrophylla* named 'WIMS RED' that is characterized by its inflorescences that emerge white in color and change to pink and finally turning red in early fall, its long panicles that are broadly conical in shape, its strong stems that are red-brown in color, its blooming period from summer to early autumn in The Netherlands, and its heat and shade tolerance.

3 Drawing Sheets

Genus/species: *Hydrangea paniculata.*
Varietal denomination: 'WIMS RED'.

BACKGROUND OF THE INVENTION

The present invention relates to a new and distinct cultivar of *Hydrangea macrophylla* and will be referred to hereafter by its cultivar name, 'WIMS RED'. 'WIMS RED' represents a new panicle *hydrangea*, a deciduous shrub grown for landscape use.

'WIMS RED' arose as part of an ongoing breeding program by the Inventor in Leende, The Netherlands with the goal of developing a new cultivar of panicle *hydrangea* with strong stems and inflorescences that change in color from white to red. 'WIMS RED' originated from a cross made in 2001 between 'Pink Diamond' (not patented) as the female parent and 'Dharuma' (not patented) as the male parent. The new *Hydrangea* was selected as a unique single plant from the progeny of the above cross in 2004.

Asexual propagation of the new cultivar was first accomplished by softwood stem cuttings in Rijkevorsel, Belgium in 2006 under the direction of the Inventor. Asexual propagation by softwood stem cuttings and tissue culture has shown that the characteristics of this cultivar are stable and reproduced true to type in successive generations.

SUMMARY OF THE INVENTION

The following traits have been repeatedly observed and represent the characteristics of the new cultivar. These attributes in combination distinguish 'WIMS RED' as a unique cultivar of *Hydrangea paniculata.*

1. 'WIMS RED' exhibits inflorescences that emerge white in color and change to pink and finally turning red in early fall.
2. 'WIMS RED' exhibits long panicle type inflorescences that are broadly conical in shape.
3. 'WIMS RED' exhibits strong stems that are red-brown in color.
4. 'WIMS RED' blooms from summer to early autumn in The Netherlands.
5. 'WIMS RED' is heat and shade tolerant.

Pink Diamond', the female parent of 'WIMS RED', differs from 'WIMS RED' in having inflorescences with sterile florets that emerge white with pink centers and turn bright pink as they mature. 'Dharuma', the male parent of 'WIMS RED', differs from 'WIMS RED' in having inflorescences with sterile florets that emerge white and turn pink as they mature and in having a more compact plant habit. 'WIMS RED' can also be compared to the cultivar 'Early Sensation' (not patented), which is similar in having inflorescences that emerge white and turn to red when mature and in having strong red-brown stems. 'Early Sensation' differs from 'WIMS RED' in having foliage that is darker in color, and in having inflorescences that are smaller and less conical in shape.

BRIEF DESCRIPTION OF THE DRAWINGS

The accompanying colored photograph illustrates the overall appearance and distinct characteristics of the new *Hydran-*

*gea*. The plant in the photograph is about three years in age as grown outdoors in a garden in Rijkevorsel, Belgium.

Figure 1:
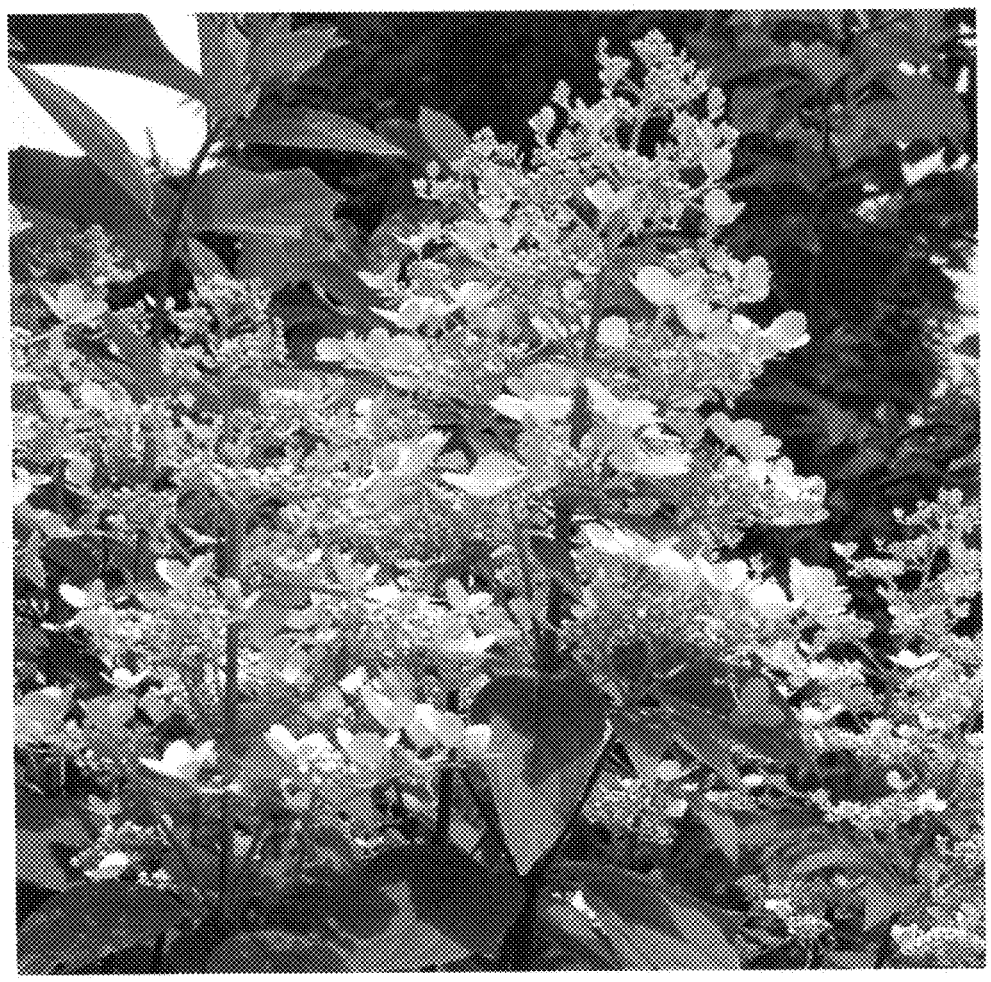

The photograph in FIG. 1 provides a view of an inflorescence of 'WIMS RED' in early summer.

Figure 2:
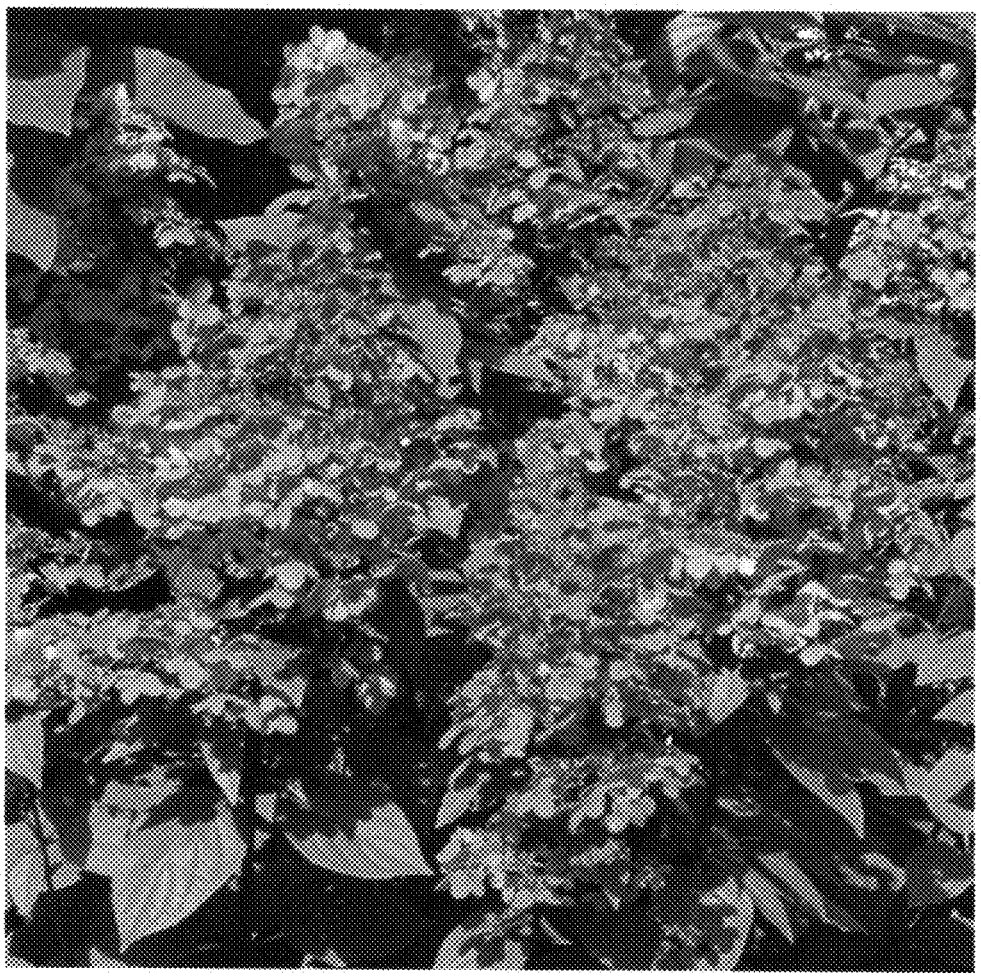

The photograph in FIG. 2 provides a view of an inflorescence of 'WIMS RED' in mid summer.

Figure 3:
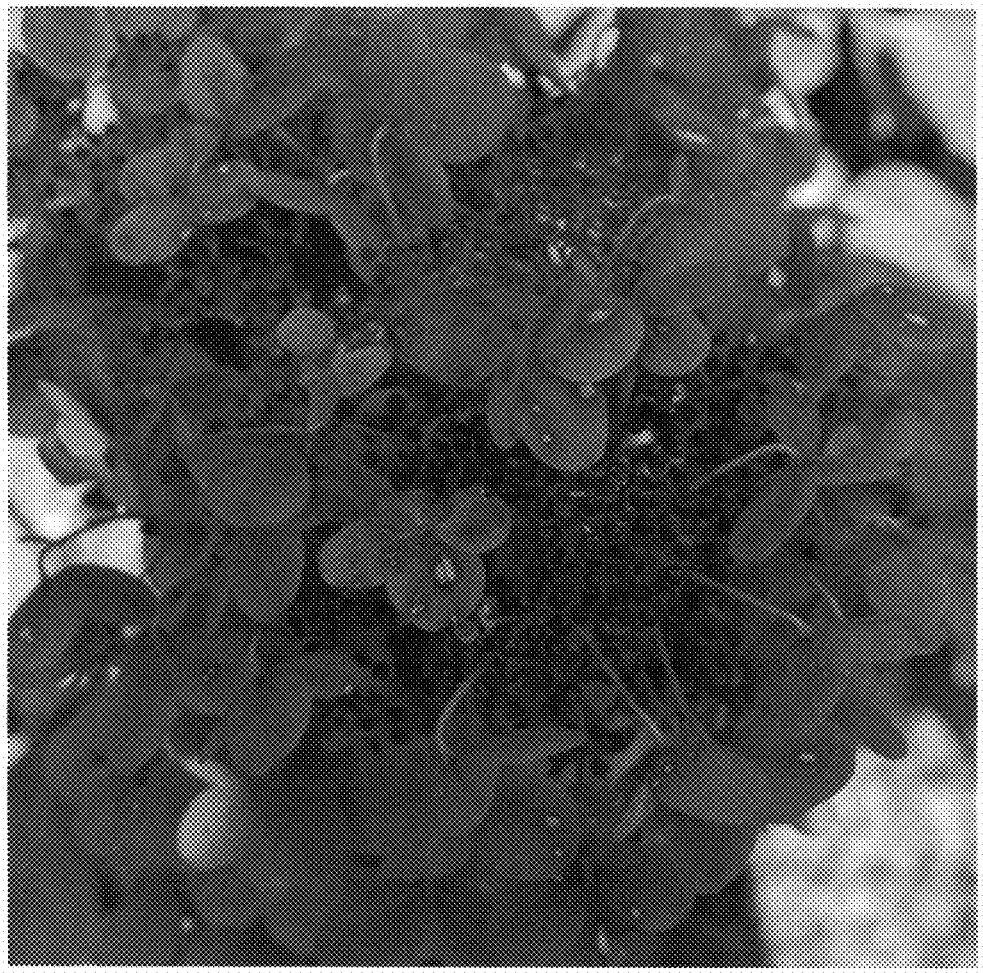

The photograph in FIG. 3 provides a view of an inflorescence of 'WIMS RED' in fall.

The colors in the photographs are as close as possible with the digital photography and printing techniques utilized and the color codes in the detailed botanical description accurately describe the new *Hydrangea*.

BOTANICAL DESCRIPTION OF THE PLANT

The following is a detailed description of four year-old plants of 'WIMS RED' as grown outdoors in 7.5-liter containers in September 2009 in Geves, Brion, France. Phenotypic differences may be observed with variations in environmental, climatic, and cultural conditions. The color determination is in accordance with The 2007 R.H.S. Colour Chart of The Royal Horticultural Society, London, England, except where general color terms of ordinary dictionary significance are used.

General description:

*Blooming period.*—About 12 weeks from summer to early autumn in The Netherlands.

*Plant habit.*—Broadly upright.

*Height and spread.*—Reaches 1.8 to 3 m in height and width in the landscape, 73 cm in height and 90 cm in width as grown in a 6.5-liter container.

*Hardiness.*—At least in U.S.D.A. Zones 3 to 8.

*Environmental stresses.*—Has shown tolerance to heat and shade.

*Diseases resistance.*—No susceptibility or disease resistance has been observed.

*Root description.*—Fibrous, dense.

*Propagation.*—Softwood stem cuttings.

*Growth rate and vigor.*—Vigorous.

Stem description:

*Stem shape.*—Round.

*Stem strength.*—Very strong.

*Stem color.*—New growth; 144C in color and tinged with 182C on sun exposed side, mature growth; 166A and sparsely covered with lenticels 5 mm in length and 1 mm in width, 1 per 3 sq cm, and 199B to 199C in color, mature bark; 199C.

*Stem size.*—Average of 38.5 cm in length (excluding peduncle) and average of 5 mm in width.

*Stem surface.*—Glabrous, dull, mature bark; moderately ridged.

*Branching.*—A four year old plant will produce 35 lateral branches, pinching improves branching.

*Internode length.*—Average of 4.5 cm.

Foliage description:

*Leaf shape.*—Ovate.

*Leaf arrangement.*—Opposite.

*Leaf division.*—Simple.

*Leaf base.*—Rounded to truncate.

*Leaf apex.*—Acute to short apiculate.

*Leaf margins.*—Serrated.

*Leaf venation.*—Pinnate, color of upper surface; 152C, color of lower surface; 145C.

*Leaf size.*—Average of 7.4 cm in length and 4.4 cm in width when mature.

*Leaf attachment.*—Petiolate.

*Leaf surface.*—Upper surface; dull and slightly rugose, moderately covered with short adpressed strigose hairs; average of 0.5 mm in length, NN155C to NN15D in color with veins covered with very short hairs; average of 0.75 mm in length, NN155C to NN155D in color, lower surface; dull and slightly ruguse, glabrous between veins, veins covered with very short hairs; average of 0.75 mm in length, NN155C to NN155D in color.

*Leaf color.*—Young foliage upper surface; 143A, young foliage lower surface; 138B, mature foliage upper surface; 137B, mature foliage lower surface; color between 138B and 147C.

*Petioles.*—Average of 9 mm in length and 2 mm in width, color; 178A to 178B on upper surface and 177D on lower surface, surface is smooth and moderately covered with lenticels 0.5 mm in length and 156D in color.

Inflorescence description:

*Inflorescence type.*—Terminal panicles that are broadly conical in shape and comprised of single sterile flowers combined with fertile flowers.

*Lastingness of inflorescence.*—Persistent with color lasting about 12 weeks.

*Inflorescence number.*—One per lateral or sublateral stem.

*Inflorescence size.*—Average of 14.3 cm in height and 12.3 cm in diameter.

*Flower number.*—An average of 80 sterile flowers per inflorescence and an average of 300 fertile flowers per inflorescence.

*Flower fragrance.*—None.

*Flower aspect.*—Upright to outward, more drooping when fading.

*Flower size.*—Sterile flowers; an average of 4.2 cm in diameter and 2 cm in depth, fertile flowers; an average of 6 mm in diameter and 4 mm in depth.

*Flower buds.*—Sterile flowers; an average of 1.4 cm in length and 8 mm in width, ovate in shape, 145D in color, glabrous surface, fertile flowers; average of 4 mm in length and 3 mm in width, ovate in shape, 157D in color with base 157B, glabrous surface.

*Flower petals.*—Sterile flowers; average of 4, rotate in arrangement, ovate, concave in shape, acute apex, cuneate base, entire margin, 3 mm in length and 1.5 mm in width, smooth and slightly glossy on both surfaces, color: upper and lower surfaces when opening; NN155D, upper surface when fully open; 155A, lower surface when fully open; NN155A, fertile flowers; average of 5, rotate in arrangement, ovate in shape, acute apex, cuneate base, entire margin, 2.5 mm in length and 1.5 mm in width, upper surface is smooth and moderately glossy, lower surface is smooth and slightly glossy, color: upper and lower surfaces when opening; NN155D, upper and lower surfaces when fully open; NN155B, colors of both surfaces on sterile and fertile flowers change to match sepal coloration changes as they age.

*Peduncles.*—Strong, extension of stem, average of 14 cm in length and 4 mm in width, 166A in color with apex 138B, surface is pubescent.

*Pedicels.*—Sterile flowers; moderate strength, an average of 1.6 cm in length and 1.5 mm in width, 157D in color, surface is dull and moderately pubescent with very short adpressed hairs, average length of hairs is 0.75 mm and NN155D in color, held between angles of 50°, fertile flowers; an average of 2 mm in length and 0.5 mm in diameter, moderate in strength, texture is smooth, dull and 145D in color.

*Sepals.*—Sterile flowers; 4 to 6 (average of 5), un-fused, slightly overlapping, rotate in arrangement, smooth and dull on both surfaces, broadly ovate to broadly obovate in shape, held nearly flat when fully open, entire margin, apex is obtuse, base is cuneate, average of 2.2 cm in length and 2.1 cm in width, color: when opening upper surface; 157D, when opening lower surface; 155A, when fully open upper surface; 150D, when fully open lower surface; between 150D and 155A, upper and lower surface fading in late summer; a blend of 62B and 62D, upper surface fading color in fall; a color between 182B and 184B, lower surface fading color in fall; 185A and flushed with 187D, fertile flowers; 5, rotate in arrangement, short triangular in shape, apex is broad acute, base is broad cuneate, margin is entire, average of 0.5 mm in length and 1 mm in width, both surfaces are smooth and slightly glossy, both surfaces when opening 157A in color, fading to a blend of 62B and 62D in late summer and 187B in fall.

*Stamens.*—Sterile flowers; average of 8, filament is an average of 2.5 mm in length and NN155C in color, anther is an average of 0.5 mm in length, kidney shaped and 156D in color, pollen is low in quantity and 156C in color, fertile flowers; average of 10, filament is an average of 3.5 mm in length and NN155C in color, anther is double kidney shaped, an average of 0.5 mm in length and 156D in color, pollen is low in quantity and 156C in color.

*Pistils.*—Fertile flowers only; average of 3, average of 2 mm in length, style is an average of 1.5 mm in length and between 157D and 150D in color, stigma is flattened on the of the style and NN155B in color.

Fruit and seed: None observed to date.

It is claimed:

1. A new and distinct cultivar of *Hydrangea* plant named 'WIMS RED' substantially as herein illustrated and described.

* * * * *